United States Patent [19]

Windeler

[11] 4,363,627
[45] Dec. 14, 1982

[54] METHOD OF FABRICATING A DENTAL PROSTHESIS

[76] Inventor: Alfred S. Windeler, 2828 Tara Trail, Xenia, Ohio 45385

[21] Appl. No.: 198,480

[22] Filed: Oct. 20, 1980

[51] Int. Cl.³ .......................... A61C 13/00; A61C 5/10
[52] U.S. Cl. ................... 433/167; 433/215; 433/223; 164/DIG. 4; 219/69 M
[58] Field of Search ............... 433/223, 222, 229, 200, 433/218, 215, 167; 164/DIG. 4; 219/69 M, 69 R, 69 E

[56] References Cited

U.S. PATENT DOCUMENTS

| | | | |
|---|---|---|---|
| 15,706 | 9/1856 | Newell | 433/200 |
| 373,348 | 11/1887 | Evans | 433/223 |
| 387,774 | 8/1888 | Diehl | 433/218 |
| 784,060 | 3/1905 | Matheret | 433/200 |
| 1,507,476 | 9/1924 | Flanigan | 433/223 |
| 2,800,566 | 7/1957 | Matulaitis | 219/69 E |
| 3,496,987 | 2/1970 | Peterson et al. | 219/69 E |
| 3,694,610 | 9/1972 | Saito et al. | 219/69 M |
| 3,934,348 | 1/1976 | Janjie | 433/223 |

OTHER PUBLICATIONS

"A Study of Some Variables Associated with Copper Plating of Dental Impressions", J. Pros. Den, Jan. 1, 1956, pp. 101–113.

Primary Examiner—Gene Mancene
Assistant Examiner—John J. Wilson
Attorney, Agent, or Firm—Louis E. Hay

[57] ABSTRACT

A metallic base dental prosthesis having an improved fit resulting from the cavity and rim portions of the prosthesis being finish machined by electric discharge machining (EDM).

1 Claim, 3 Drawing Figures

U.S. Patent     Dec. 14, 1982     4,363,627
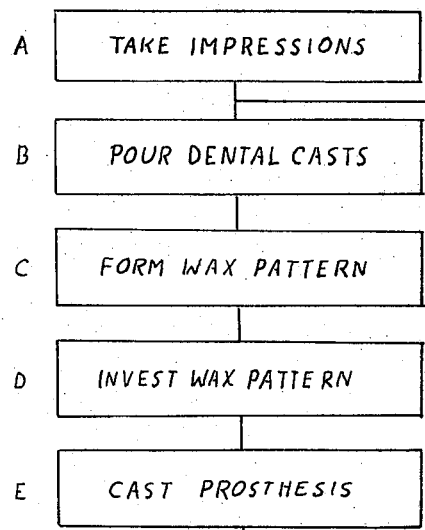
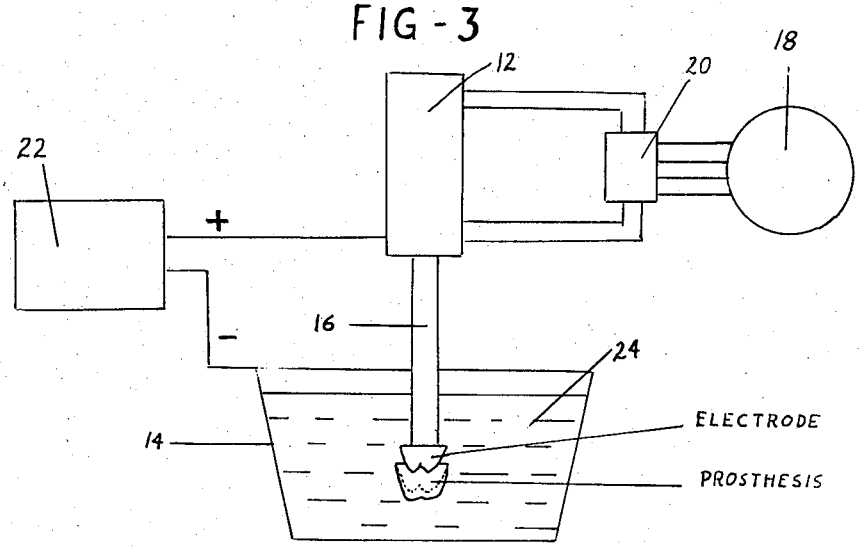

METHOD OF FABRICATING A DENTAL PROSTHESIS

BACKGROUND OF THE INVENTION

This invention relates to the field of prosthetic dentistry, and more specifically to the fabrication and fitting of partial fixed and removable dentures such as crowns and bridges.

Prostheses made in accordance with the well established technique only approximate an ideal fit, for which reason the useful life, or the ability to preserve the life of the teeth to which affixed is also limited. The principal problem is the inability to produce a prosthesis which will perfectly fit the prepared surfaces of a tooth.

The best results under the established technique are obtained with alloys containing a high content of a noble metal such as gold. Unfortunately, the advantages are counterbalanced by the disadvantage of very high cost.

Other and cheaper alloys such as chrome-cobalt or chrome-nickel are in common use for the fabrication of dental prostheses. The problem with the cheaper alloys is the same as in many other arts; that is, nothing works as well as gold.

The principal problem is one of misfit, especially where the edge of the prosthesis meets the margin of the prepared tooth. The better the fit between the prosthesis and the prepared tooth surfaces, the less likely bacteria can enter and destroy the tooth. It is rather common that the patient will not even suspect that anything is wrong until the prosthesis becomes detached, at which time it is discovered that the tooth has decayed under the prosthesis and may well be beyond further repair.

The misfit between a prosthesis and the supporting surfaces on a tooth cannot be corrected by the cement holding it in place. The cement or luting agent may appear to be a fix; however, it is soluble in oral fluids and will eventually admit bacteria.

SUMMARY OF THE INVENTION

The present invention has for its primary objective the reduction of the misfit of a conventionally fabricated prosthesis, such as a crown, for example, by taking such prosthesis and improving the fit by machining the surfaces which are to be contiguous to the prepared tooth surfaces by electric discharge machining(EDM).

BRIEF DESCRIPTION OF THE DRAWINGS

FIG. 1 is a block diagram showing the basic steps in the construction of a metallic base prosthesis in accordance with the conventional technique;

FIG. 2 is a block diagram functionally tied to the steps depicted in FIG. 1 and showing the intermingling of additional and novel steps to create an improved fitting prosthesis; and, FIG. 3 is a schematic showing a cast metallic prosthesis positioned in an electric discharge machine in proper position for final machining.

DESCRIPTION OF THE PREFERRED EMBODIMENT

For purposes of illustration only, it will be presumed that a crown is to be constructed. Since the basic steps in the fabrication of a dental crown, as depicted in FIG. 1, are also used in the fabrication of a crown in accordance with the present invention, all steps will be briefly described.

When a patient has a tooth which is to be fitted with a metallic crown either because the tooth is badly decayed, or a portion thereof was broken away because of an injury, the dentist cuts away that portion of the tooth which is to be replaced by the crown. The outside of the crown is to be substantially the shape of the natural tooth before it become severely decayed or suffered the injury. The dentist removes a portion of the tooth over the entire circumference in most cases, and also the occlusal surface, to leave a central post which bevels outward near the gum line. The actual steps in the fabrication and fitting of a crown commence after preparation of the tooth to be crowned or repaired.

The first step (FIG. 1, Step A) is to take impressions of the patient's upper and lower dental arches in a suitable moldable material in impression trays. Suitable impression materials are well known in the dental art. The impressions are female molds or negative replicas of the patient's dental arches.

The second step (FIG. 1, Step B) is to form dental casts which are positive replicas of the patient's dental arches. The dental casts are formed of a gypsum material having good dimensional stability in order to form accurate replicas. The dental casts are formed from the impressions taken in Step A above. The technique for making dental casts is well known, and is graphically illustrated and described in U.S. Pat. No. 3,975,489 Mercer.

The dental casts are next mounted in an articulator in a manner to have the casts in their centric occlusal position; that is, the teeth on the dental casts are in the same relative position as the teeth in the patient's mouth. For illustrative purposes only, it will be assumed that a lower bicuspid is to be crowned; hence, there will be a gap between the lower bicuspid to be crowned and its mating upper bicuspid.

The next step (FIG. 1, Step C) is to form a wax pattern of the crown to be fabricated. The wax pattern is constructed on the replica of the prepared tooth on the lower dental cast. The outside of the wax pattern is shaped to fit the adjacent lower teeth, while the inside portion of the wax is contiguous with the prepared surface of the tooth. The occlusal surface on the wax pattern is formed to fit the cusps on the mating upper bicuspid. It is thus noted that all the material removed in preparation of the tooth to be restored has been replaced with wax. Theoretically at least, if the crown can be built to the exact shape and size of the wax pattern, when the crown is cemented in place, the restored tooth will be a replica of the original tooth.

The next step (FIG. 1, Step D) is to very carefully remove the wax pattern from the lower dental cast and to invert it in a refractory material. The refractory material is usually a material which has been specially formulated to withstand the thermal shock of sudden exposure to high temperature molten metal. A sprue is formed of wax and joined to the wax pattern. The sprue forms the passage through which the wax pattern is evaporated, and also the passage through which the molten metal enters the cavity formed by the evaporated wax pattern. After the refractory material has set, the assembly is heated to about 900 degrees F. which will vaporize the wax and leave a cavity mold which is a negative replica of the crown to be cast in the next step below. It is noted that the outside of the cavity mold is comparable to the outside configuration of the desired crown, and that there is an inner portion which is comparable to the prepared surface of the tooth extending downward into the cavity mold.

The next step (FIG. 1, Step E) is to mount the refractory mold in a centrifugal casting machine such as is used in most dental laboratories. An alloy slug is heated to the proper temperature and the molten metal is shot into the mold where it is allowed to harden and cool down. At the proper time the refractory material is broken away from the cast crown.

After the rough crown has been removed, it is cleaned and polished. It is then fitted in place on the dental cast by removing high spots as necessary. The crown is also articulated and corrected as necessary to make certain there is no cusp interference when the lower jaw is manipulated.

The crown is next fitted to the tooth in the patient's mouth. If an acceptable fit has been attained, the crown is cemented to the tooth to complete the restoration.

Many times a porcelain facing is placed on the visible portion of the crown for asthetic reasons. The powered porcelain is mixed with water and applied to the crown as a paste. The combination is then heated to a temperature slightly below the melting point of the metal, at which temperature the porcelain fuses to the metal. This process frequently induces distortion in the casting as the porcelain-metal sandwich cools. The two materials have different shrinkage factors and at the present time it is not possible to prevent introduction of this type of shrinkage error. As will be further discussed below, the machining technique of the present invention will be found of particular value on crowns having porcelain facings.

There are variations of the above-described technique for forming dental crowns. These variations result from various factors such as the complexity of the crown, the general condition of the patient's teeth, whether or not the crown is to be on a visible tooth, the amount of money a patient wishes to spend, and the preference of the dentist. For example, in some situations the dentist may not take full impressions, or, he may not articulate the crown before fitting it to the patient.

Within the scope of the present invention, the steps outlined in FIG. 1 include any and all variations and modifications of the basic steps as described, since the particular descriptions are for illustrative purposes only.

An ideally fitting metallic crown would have a uniform clearance of about 0.001 inch on the prepared tooth surface to which it is to be cemented. This ideal fit is rarely achieved and there is no known method by which this variable clearance may be measured. The error is a cumulative error produced by the various transfer steps and by the shrinkage and distortion errors which cannot be avoided. when a poorly fitted crown is cemented in place, the longevity of the tooth is severely compromised. All cementing materials are soluble in saliva, and as they are leeched out from the interface between the crown and the tooth, a gap is formed which harbors bacteria which attacks the tooth structure.

Since the problem of poorly fitting crowns cannot be overcome by any cement known or used by the dental profession, the only avenue of attack is to produce superior fitting crowns. Extensive testing of crowns made by the technique described below established that crowns finally machined by EDM do produce superior fitting crowns. The tests were comparative tests in which a crown which had been carefully fabricated in the conventional manner and its fit on a prepared surface noted, was then further machined by EDM and its new fit noted. A misfitting crown having distortion will usually not go "home" on the prepared surface until the high spot restrictions are removed. These restrictions are usually invisible to the eye and are hard to find, and it is also difficult not to remove an excess amount of material which would produce a gap.

FIG. 2 depicts the steps added by the new technique and their relationship to the steps of the conventional technique.

The first additional step (FIG. 2, Step X) consists of making a suitable electrode. Although the electrode may be formed within the cavity mold of the impression (FIG. 1, Step A), it is recommended that the electrode be formed in a second impression taken at the time the first impression is made within the patient's mouth. By using a second impression, it is assured that there will be no distortion during removal of the hardened dental cast (FIG. 1, Step B) which would affect the accuracy of the electrode. There is no way for measuring distortion, and the fact that there was distortion will not be discovered prior to fitting the crown to the prepared surface on the patient's tooth.

Regardless as to whether or not a second impression is used, the material used to form the impression in which the electrode is to be formed must be one which is dimensionally stable for the time required to form the electrode. Such impression materials are readily available from dental supply companies.

The electrode is formed by electroforming copper into the cavity mold of the impression. Since the material used in forming the impression is a dielectric, the impression, and especially that portion in which the electrode is to be formed, must be made conductive by coating it with a very thin film of silver. The silver film is so thin that its thickness may be disregarded. There are techniques for applying the silver film, a few of which are described in the article A Study of Some Variables Associated With Copperplating of Dental Impressions, pages 101–113 of the January 1956 issue of the Journal of Prosthetic Dentistry.

Dental impressions were often plated about 30 years ago in order to produce less abrasive dental casts; however, this procedure is no longer necessary because superior gypsum materials have been subsequently developed and are in current use. The copper plating was an integral part of the dental cast and provided a metallic non-sloughing surface. The copper plating did not require an appreciable thickness since it was to be filled with hardened gypsum. The plated dental cast formed the base on which a wax pattern was to be constructed as in FIG. 1, Step C; whereas, the present plating consideration relates to FIG. 1, Step X.

In forming the electrode to be used with the present invention, after the dental impression has been provided with the electrically conductive silver film, the impression is submerged in an acid copper plating bath. The electrode is allowed to build to a thickness on the order of 0.020 inch, which was found to be of sufficient structural rigidity for its required purpose since the electrode is of relatively small size.

After the electrode has been allowed to build to the desired thickness in the plating bath it is removed and the open end of the electrode is soldered to an axially extending metallic rod, and the electrode-rod assembly is now ready for mounting in the ram of the EDM apparatus.

Specific reference is now made to FIG. 3 which is schematic depicts the principal elements of the final machining apparatus 10. The apparatus 10 has a hydraulic ram 12 and a work tank 14 which are mounted on a common frame (not shown). The electrode-rod 16 is removably attached to the hydraulic ram which controls its vertical position on command. The hydraulic ram is powered by a hydraulic pump 18 through a servo valve 20 in series with the required hydraulic lines as depicted in FIG. 3. The crown is releasably supported in a suitable holding fixture (not shown for clarity) at the bottom of the work tank. The crown must be supported to be in vertical alignment with the electrode.

The EDM power source 22 is connected so that the electrode is positive and the crown is negative. The particular EDM power source used was a model 150B manufactured by Hansvedt Engineering Inc. at Urbana Ill. Other power sources are available.

If the crown is cast of a chrome-cobalt alloy, it was found that the EDM operation is performed in a satisfactory manner at about 2 amperes and a frequency of 8000 Hz., and with the power on for 80 percent of the time and off for 20 percent of the time. Other alloys may require variations of the electrical output.

The EDM operation is performed in a suitable liquid dielectric 24 which is added to the tank after the cast crown and the electrode are aligned. Kerosene was used; however, other dielectrics may be used. The crown is machined to have about 0.001 inch clearance between the electrode and the cavity in the crown. This clearance will provide a thin and uniform thickness of the luting cement with which the crown is attached to the prepared surfaces on the patient's tooth.

Although theoretically not as accurate as making the electrode in an original impression, the electrode may also be made in an impression taken on a dental cast. This situation may occur when the dentist takes the impressions and also pours the dental casts. Only the hardened dental casts would be sent to the dental laboratory, and the impressions would be discarded by the dentist. It would now become necessary for the laboratory to take an impression of the hardened dental cast in order to construct the electrode. Within the scope of the present invention, the term "impression" is a negative replica of a patient's dental arch including the teeth, whether taken in the mouth or on a dental cast poured in the original impression.

Although a crown was used as an illustrative example of a prosthesis made in accordance with the present invention, within the scope of the invention, the term "dental prosthesis" encompasses all metallic base dentures having a cavity portion to engage a comparable male portion within a patient's mouth, and also fixed metallic base partial dentures such as a bridge joined to an adjacent tooth or teeth on both sides of one or more missing natural teeth, and removable metallic base partial dentures held in position by means of clasps.

It is to be understood that the embodiments of the present invention as shown and described are to be regarded merely as illustrative, and that the invention is susceptible to variations, modifications and changes without regard to construction methods, within the scope of the appended claims.

I claim:

1. A method of fabricating a dental prosthesis, at least the major portion of which is a metallic element configured for wearing in contact with a finite area within the oral cavity of a patient, said method comprising the steps:

(a) fabricating a rough cast prosthesis by the steps:

(a-1) pouring an upper and a lower dental cast in impressions taken in the oral cavity of a patient, one of said dental casts including the finite area in contact with which said prosthesis is to be worn;

(a-2) mounting said dental casts in a dental articulator and hand forming a wax pattern over the finite area on said dental cast to the desired configuration of said rough cast prosthesis;

(a-3) removing said wax pattern from said dental cast and investing said wax pattern in a pliable refractory material, and, after the refractory material has solidified, elevating the ambient temperature surrounding said refractory material to evaporate said wax pattern to leave a cavity mold in said refractory material;

(a-4) casting a rough prosthesis in said cavity mold by injecting a high temperature molten metal which is allowed to solidify into said rough cast prosthesis which is then removed from said cavity mold;

(b) forming an accurate metallic electrode by electroforming a metal into an impression taken in the oral cavity of said patient, said electrode to be configured to the finite area in the oral cavity of said patient in contact with which said prosthesis is to be worn; and, (c) in an electric discharge machine, mounting said rough cast prosthesis and said electrode in linear spaced alignment with said electrode in alignment with the corresponding finite area of said rough prosthesis, and finish machining said finite area of said rough prosthesis to the configuration of said electrode by electric discharge machining.

* * * * *